United States Patent [19]

Fisher et al.

[11] Patent Number: 5,593,649

[45] Date of Patent: Jan. 14, 1997

[54] CANISTER WITH PLASMA GAS MIXTURE FOR STERILIZER

[75] Inventors: Jim Fisher, Hawthorne, Ill.; Bryant A. Campbell, deceased, late of Los Gatos, Calif., by Louise A. Campbell, legal representative; Kern A. Moulton, Reno, Nev.

[73] Assignee: Abtox, Inc., Mundelein, Ill.

[21] Appl. No.: 462,982

[22] Filed: Jun. 5, 1995

Related U.S. Application Data

[63] Continuation-in-part of Ser. No. 213,613, Mar. 21, 1994, Pat. No. 5,472,664, which is a continuation-in-part of Ser. No. 73,653, Jun. 7, 1993, Pat. No. 5,413,759, which is a continuation of Ser. No. 817,714, Jan. 7, 1992, abandoned, which is a division of Ser. No. 576,292, Aug. 31, 1990, Pat. No. 5,115,166, which is a continuation-in-part of Ser. No. 475,602, Feb. 6, 1990, abandoned, which is a continuation-in-part of Ser. No. 321,483, Mar. 8, 1989, abandoned.

[51] Int. Cl.$^6$ ............................................ A61L 9/00
[52] U.S. Cl. ........................ 422/305; 206/6; 206/213.1; 220/581; 422/292; 422/295; 422/906
[58] Field of Search ............................ 422/23, 40, 292, 422/295, 305, 906, 307; 206/6, 213.1; 220/581

[56] References Cited

U.S. PATENT DOCUMENTS

| | | |
|---|---|---|
| 2,426,630 | 9/1947 | Mapes .................................. 206/6 X |
| 3,132,618 | 5/1964 | Andrews et al. ................... 220/581 X |
| 3,383,163 | 5/1968 | Menashi . |
| 3,410,776 | 11/1968 | Bersin . |
| 3,428,548 | 2/1969 | Hollahan . |
| 3,547,802 | 12/1970 | Gleit et al. . |
| 3,647,676 | 3/1972 | Bersin . |
| 3,704,096 | 11/1972 | Verses et al. . |
| 3,737,608 | 6/1973 | Nagao et al. . |
| 3,851,436 | 12/1974 | Fraser et al. . |
| 3,948,601 | 4/1976 | Fraser et al. . |
| 4,065,369 | 12/1977 | Ogawa et al. . |
| 4,123,663 | 10/1978 | Horiike . |
| 4,138,306 | 2/1979 | Niwa . |
| 4,151,034 | 4/1979 | Yamamoto et al. . |
| 4,160,690 | 7/1979 | Shibagaki et al. . |
| 4,169,123 | 9/1979 | Moore et al. . |
| 4,169,124 | 9/1979 | Forstrom et al. . |
| 4,207,286 | 6/1980 | Gut Boucher . |
| 4,230,663 | 10/1980 | Forstrom et al. . |
| 4,289,728 | 9/1981 | Peel et al. . |
| 4,321,232 | 3/1982 | Bithell ..................................... 422/23 |
| 4,348,357 | 9/1982 | Bithell ..................................... 422/23 |
| 4,366,125 | 12/1982 | Kodera et al. ......................... 422/295 |

(List continued on next page.)

FOREIGN PATENT DOCUMENTS

| | | |
|---|---|---|
| 0109352 | 5/1984 | European Pat. Off. . |
| 0387022 | 9/1990 | European Pat. Off. . |
| 0474137 | 3/1992 | European Pat. Off. . |
| 268396 | 5/1989 | Germany . |
| 525607 | 5/1977 | Japan . |
| 58-87825 | 5/1983 | Japan . |
| 58-103460 | 6/1983 | Japan . |
| 58-162276 | 9/1983 | Japan . |
| 2214081 | 1/1989 | United Kingdom . |
| 2253144 | 9/1992 | United Kingdom . |
| 92/15336 | 9/1992 | WIPO . |

OTHER PUBLICATIONS

Caputo, "Alternative Sterilization Technologies Come of Age," *Medical Device and Diagnostic Industry*, 14(12), pp. 41–42 (1992).

(List continued on next page.)

*Primary Examiner*—Robert J. Warden
*Assistant Examiner*—Krisanne M. Thornton
*Attorney, Agent, or Firm*—Majestic, Parsons, Siebert & Hsue

[57] ABSTRACT

A canister is provided that is adapted for use in a plasma induced sterilization process. The canister contains a gas mixture that is pressurized to between about 2200 psig to about 2500 psig. The gas mixture has about 2.0 to 2.4 (v/v) percent hydrogen and about 2.6 to 3.0 (v/v) percent oxygen, and the rest of the gas mixture is noble gas or a mixture of noble gases.

3 Claims, 12 Drawing Sheets

U.S. PATENT DOCUMENTS

| | | | |
|---|---|---|---|
| 4,437,567 | 3/1984 | Jeng | 206/210 |
| 4,590,042 | 5/1986 | Drage | 422/186.06 |
| 4,600,563 | 7/1986 | Diederich | 422/186.29 |
| 4,640,782 | 2/1987 | Burleson | 210/748 |
| 4,643,876 | 2/1987 | Jacobs et al. | 422/23 |
| 4,711,767 | 12/1987 | Diederich | 422/186.29 |
| 4,801,427 | 1/1989 | Jacob | 422/23 |
| 4,818,488 | 4/1989 | Jacob | 422/23 |
| 4,884,708 | 12/1989 | Lange et al. | 206/6 X |
| 4,898,715 | 2/1990 | Jacob | 422/23 |
| 4,917,586 | 4/1990 | Jacob | 422/23 |
| 4,931,261 | 5/1990 | Jacob | 422/292 |
| 4,943,417 | 7/1990 | Jacob | 422/292 |
| 4,976,920 | 12/1990 | Jacob | 422/23 |
| 5,084,239 | 1/1992 | Moulton et al. | 422/22 |
| 5,171,525 | 12/1992 | Jacob | 422/23 |
| 5,185,132 | 2/1993 | Horiike et al. | 422/186.5 |
| 5,215,636 | 6/1993 | Danilychev et al. | 204/164 |
| 5,244,629 | 9/1993 | Caputo et al. | 422/23 |
| 5,290,489 | 3/1994 | Williams et al. | 264/22 |
| 5,424,103 | 6/1995 | Ahn | 427/569 |

OTHER PUBLICATIONS

Caputo et al., "Validation Testing of a Gas Plasma Sterilization System," *Medical Device and Diagnostic Industry*, 15(1), pp. 132–138 (1993).

Chapman, "Gas Phase Collision Processes," Chpt. 2 in *Glow Discharge Processes*, A Wiley–Interscience Publication, New York: John Wiley & Sons, pp. 21–48 (1980).

Hollahan, Letter to the Editor, *Journal of Chemical Education*, 43(7), p. 392 (1966).

Hollahan, "Applications of Low–Temperature Plasmas to Chemical and Physical Analysis," Chpt. 7 in *Techniques and Applications of Plasma Chemistry*, (Hollahan, ed.), New York: John Wiley & Sons (1974).

Fraser et al., "Plasma Sterilization Technology for Spacecraft Applications," (NASA–CR–146314), Final Report (Boeing Co., Seattle, Washington), Sep. 1975.

"Cold Sterilization Beyond 1995: A Look at Alternatives to Dec. 1988 EtO," *Journal of Healthcare Material Management*, 10(8), Sep. 1992.

Leaper, "Comparison of the Resistance to Hydrogen Peroxide of Wet and Dry Spores of *Bacillus subtilis* SA22," *Journal of Food Technology*, 19, pp. 695–702 (1984).

Leaper, "Influence of Temperature on the Synergistic Sporicidal Effect of Peracetic Acid Plus Hydrogen Peroxide on *Bacillus subtilis* SA22 (NCA 72–52)," *Food Microbiology*, 1, pp. 199–203 (1984).

Leaper, "Synergistic Killing of Spores of *Bacillus subtilis* by Peracetic Acid and Alcohol," *Journal of Food Technology*, 19, pp. 355–360 (1984).

Leaper et al., "A Note of the Effect of Storage on the chemical Resistance of Spores of *Bacillus subtilis* SA22 and *Bacillus subtilis globigii* B17," *Journal of Applied Bacteriology*, 64, pp. 183–186 (1988).

Hollahan, "Analytical Applications of Electrodelessly Discharged Gases," *Journal of Chemical Education*, 43(5), pp. A401–A416 (1966).

Holahan, "Research with Electrodelessly Discharged Gases," *Journal of Chemical Education*, 43(6), pp. A497–A512 (1966).

Rudder et al., "Remote Plasma–Enhanced Chemical–Vapor Deposition of Epitaxial Ge Films," *Journal of Applied Physics*, 60(10), pp. 3519–3522 (1986).

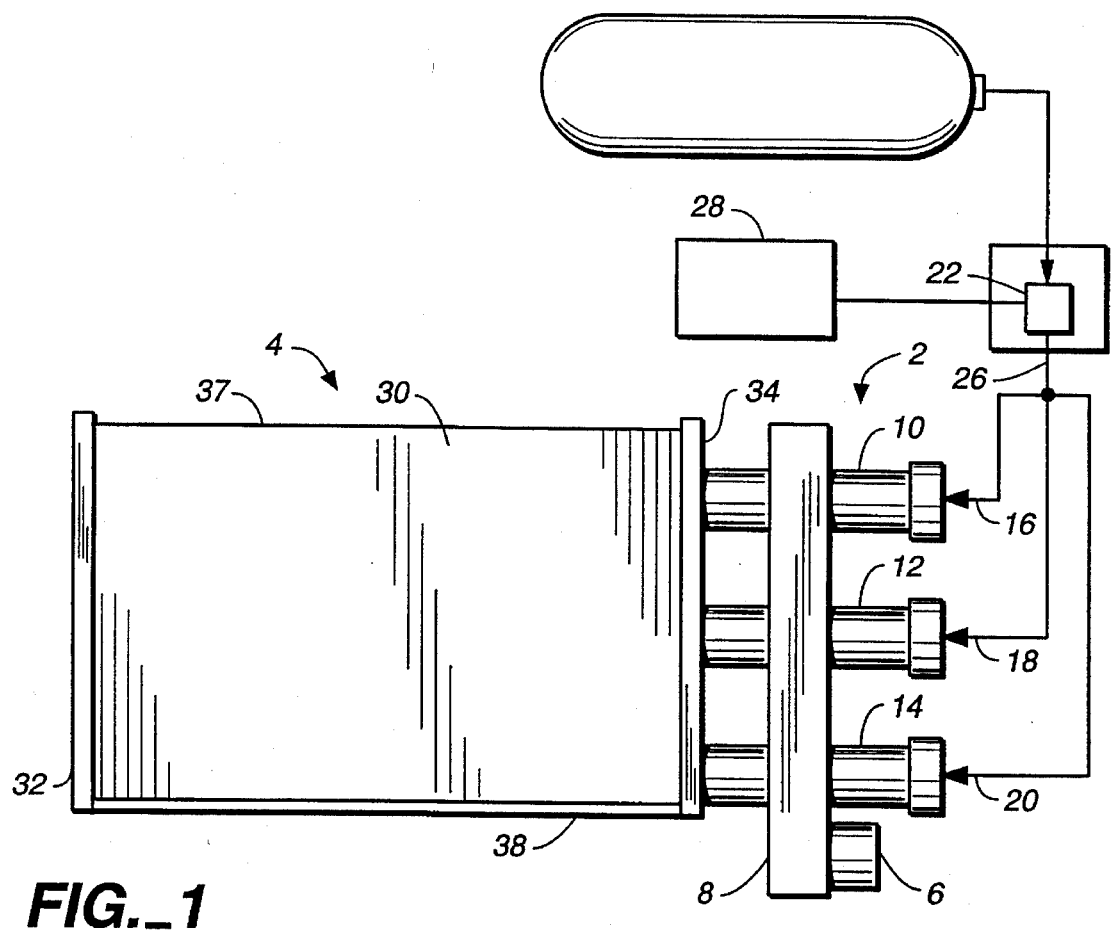
FIG._1
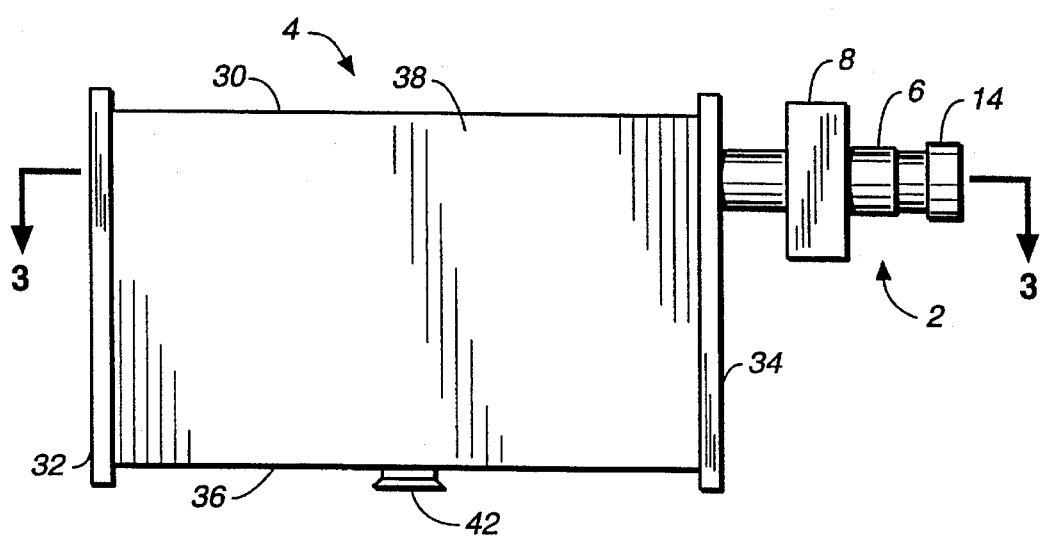
FIG._2

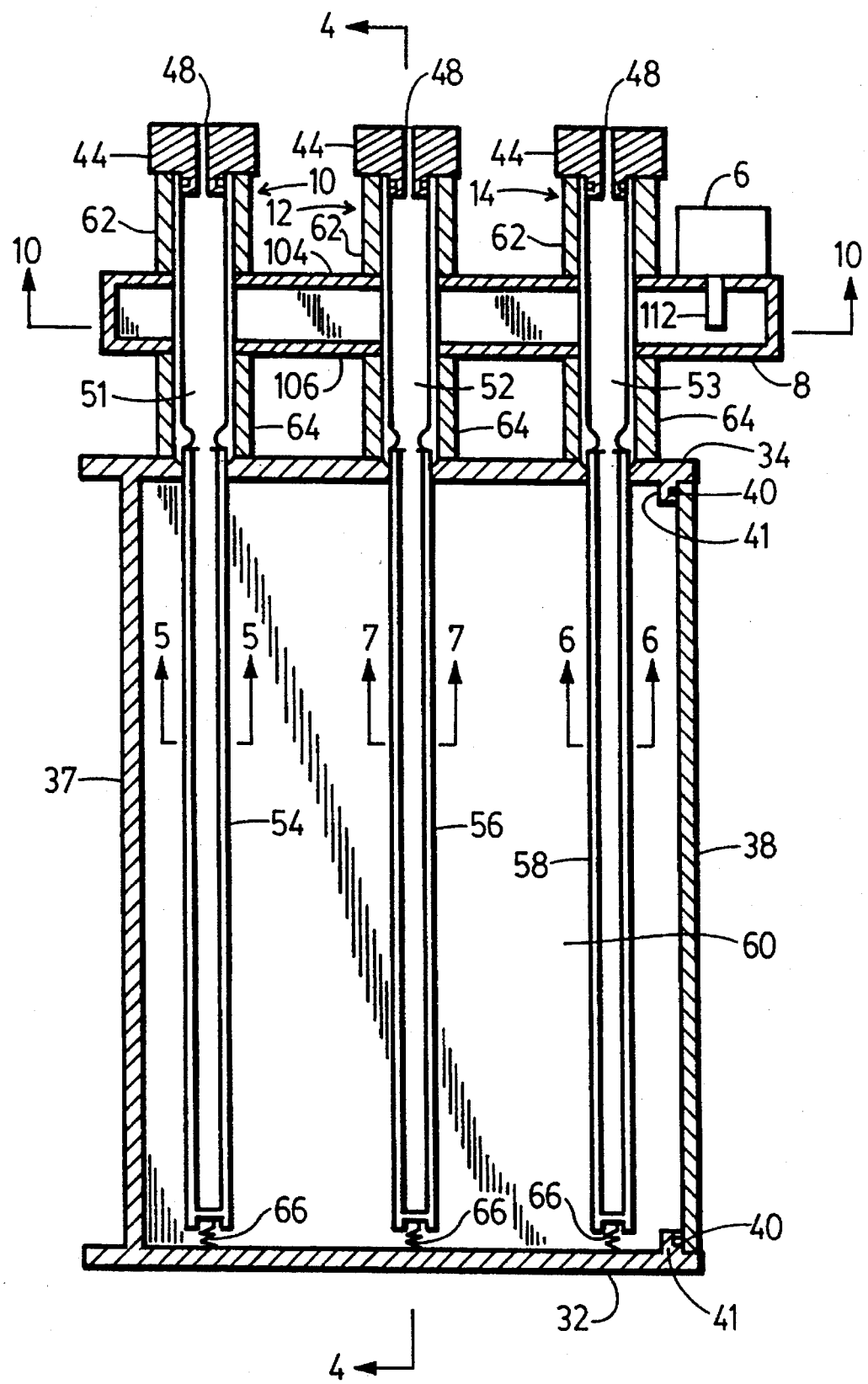
FIG._3.

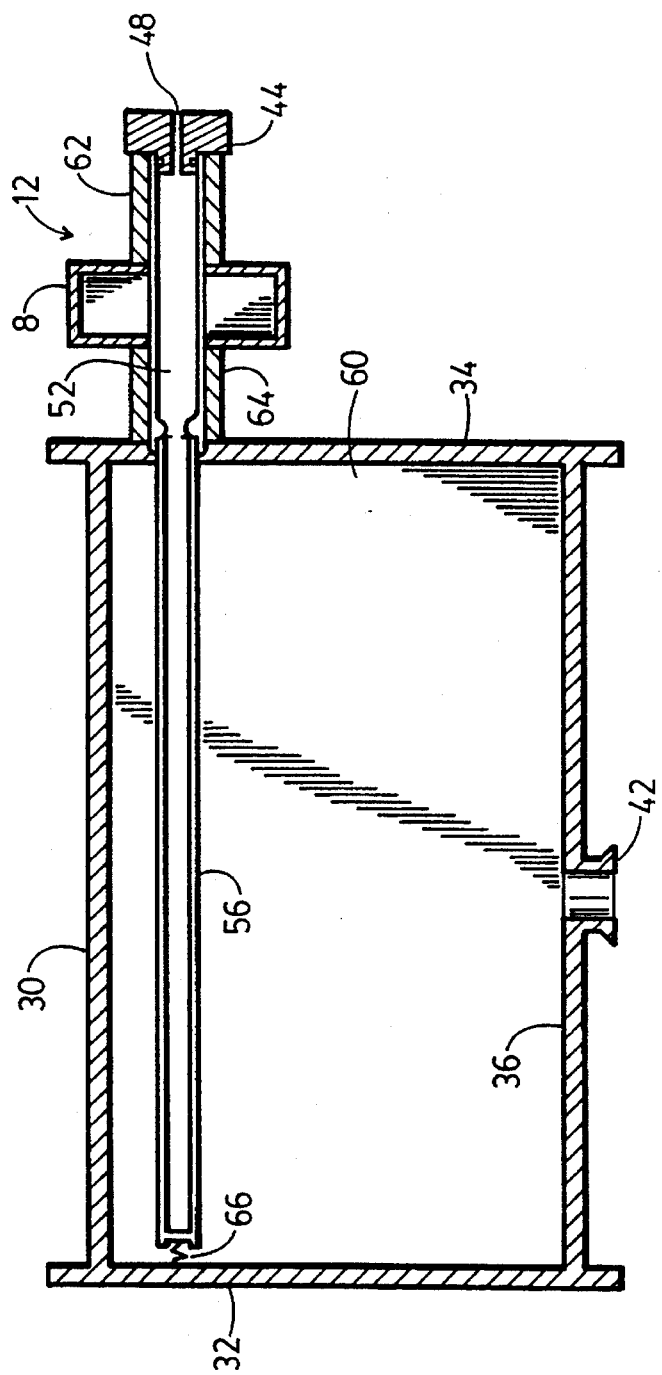
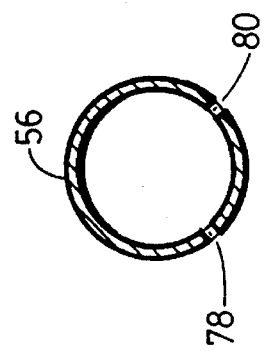
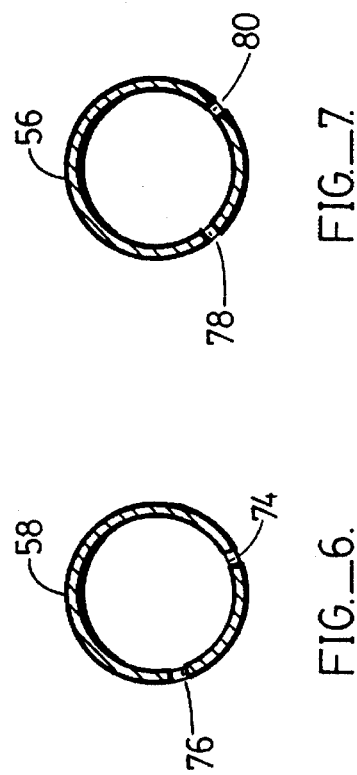
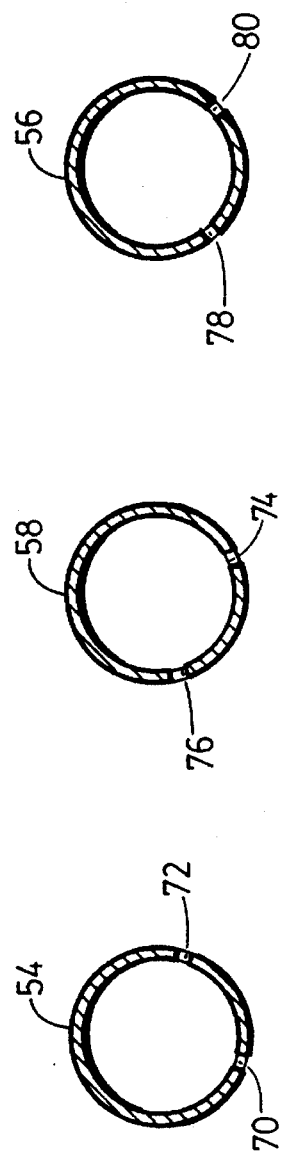
FIG._4.
FIG._5.
FIG._6.
FIG._7.

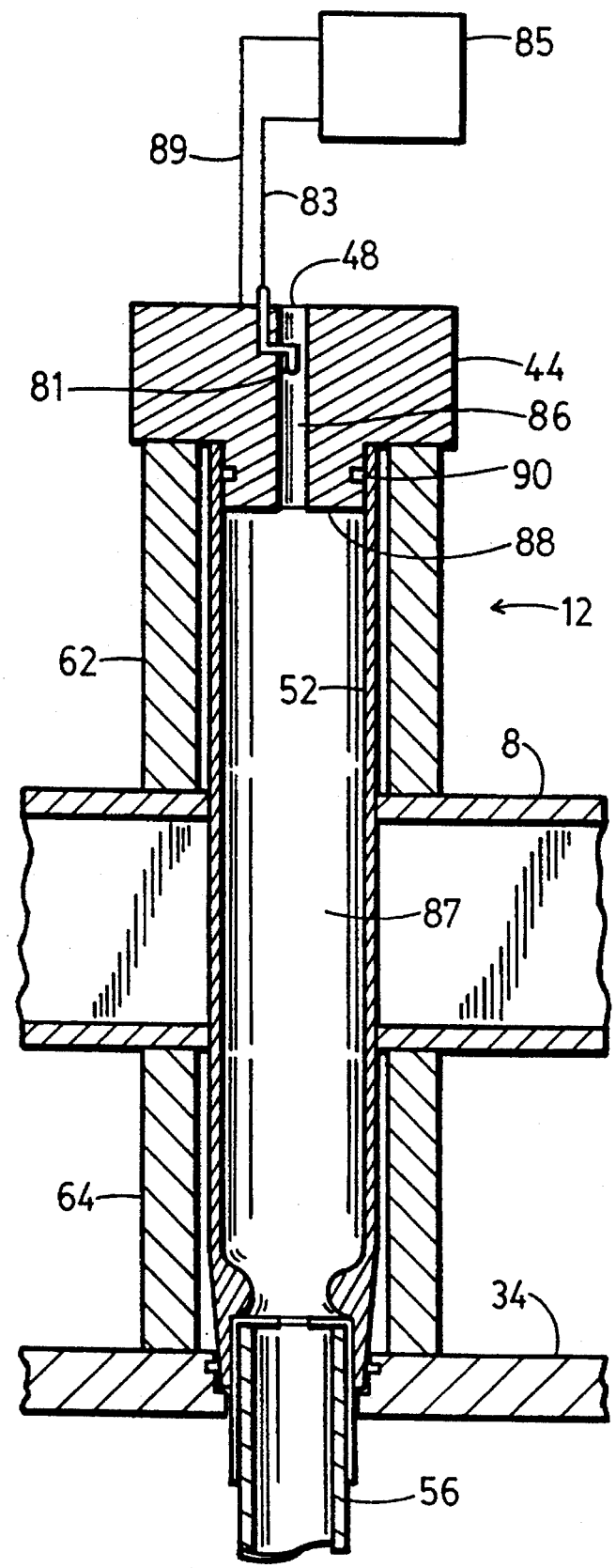
FIG._8.

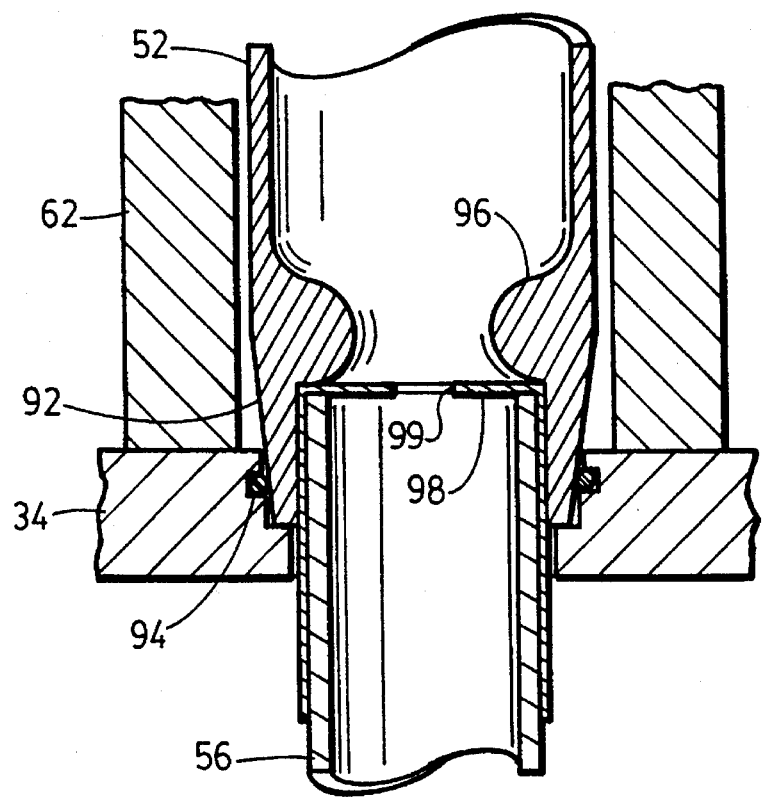
FIG._9.
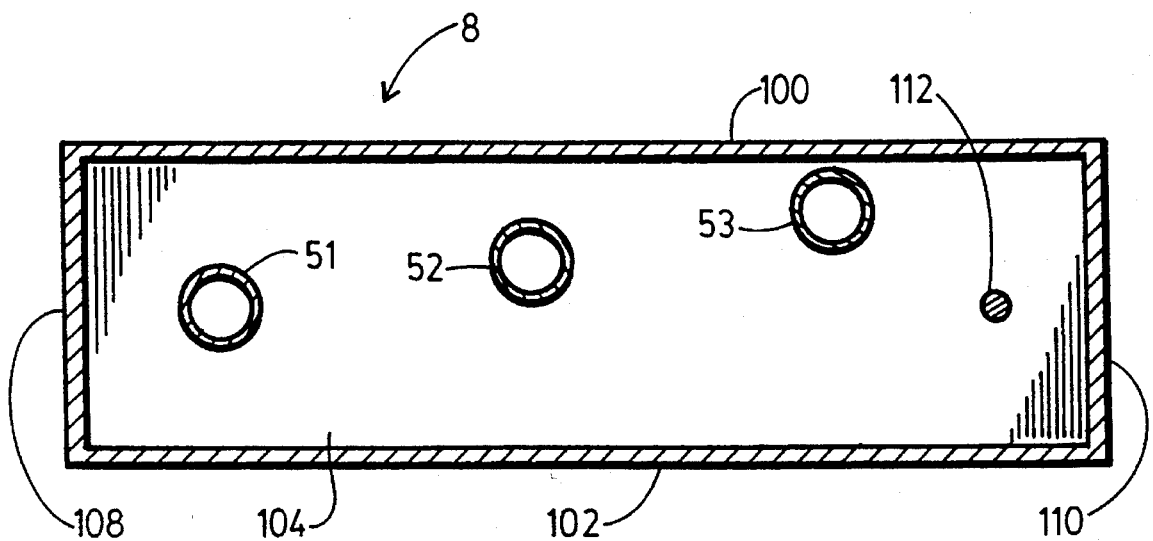
FIG._10.

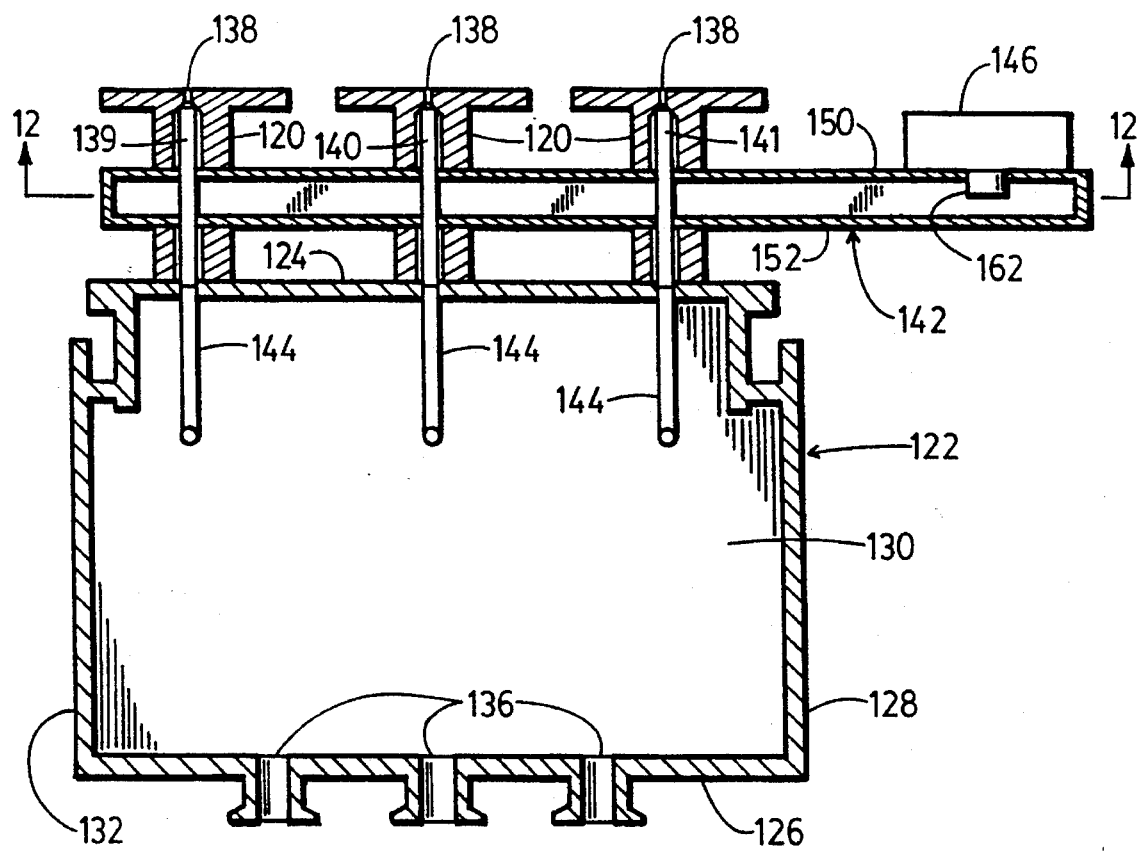
FIG._11.
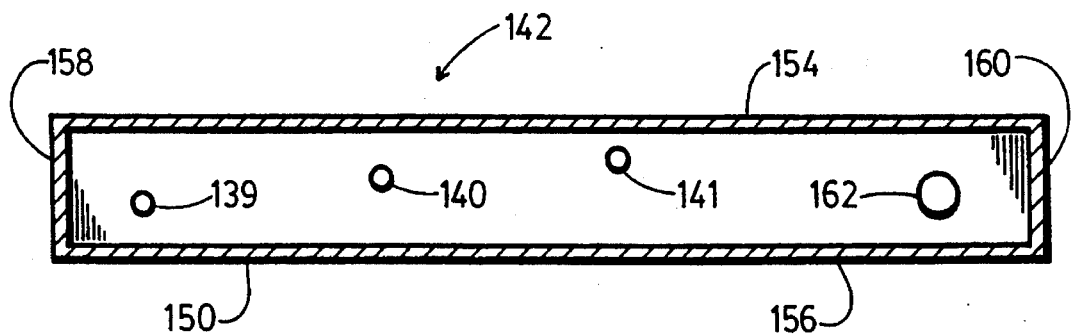
FIG._12.

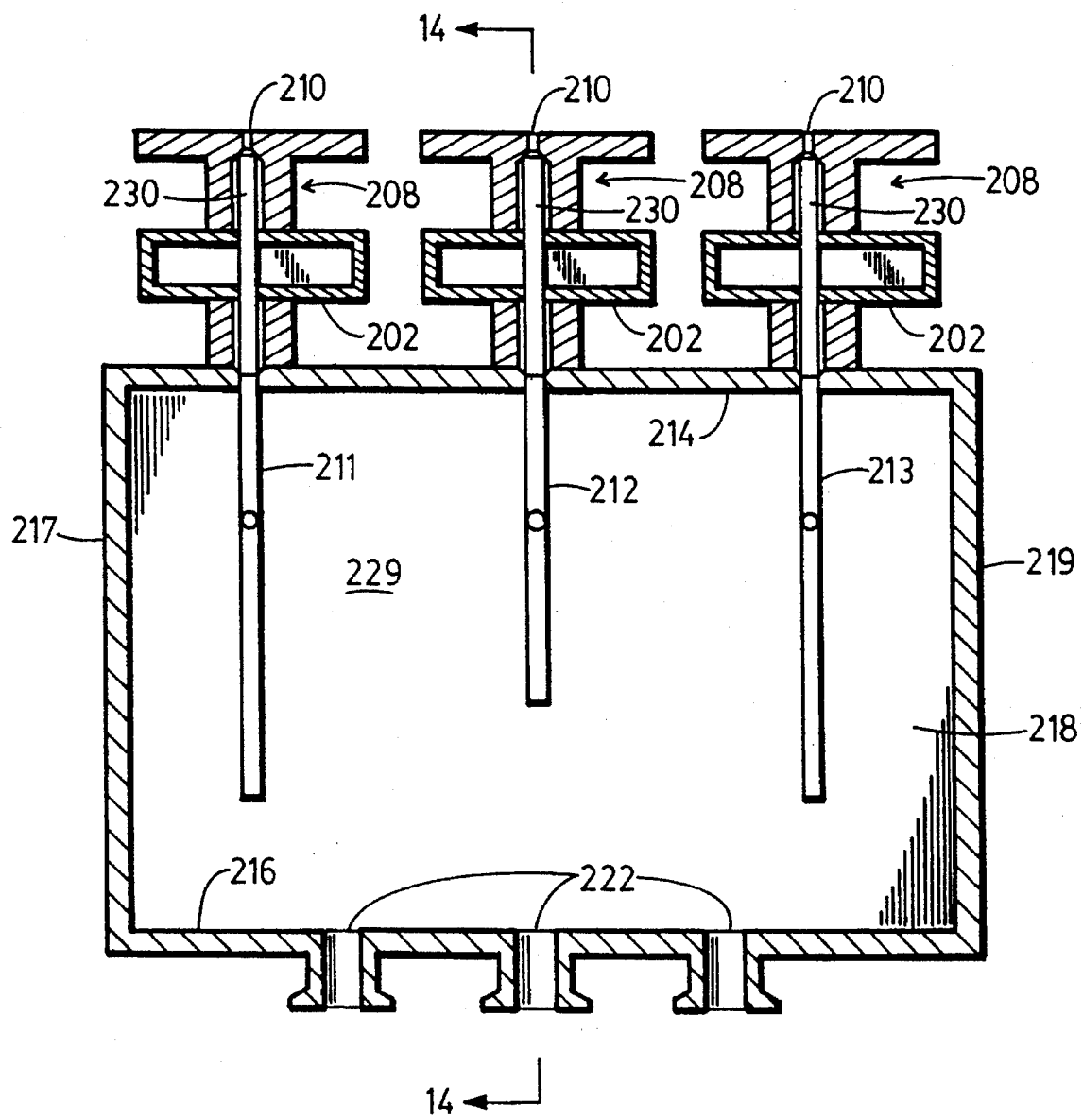
FIG._13.

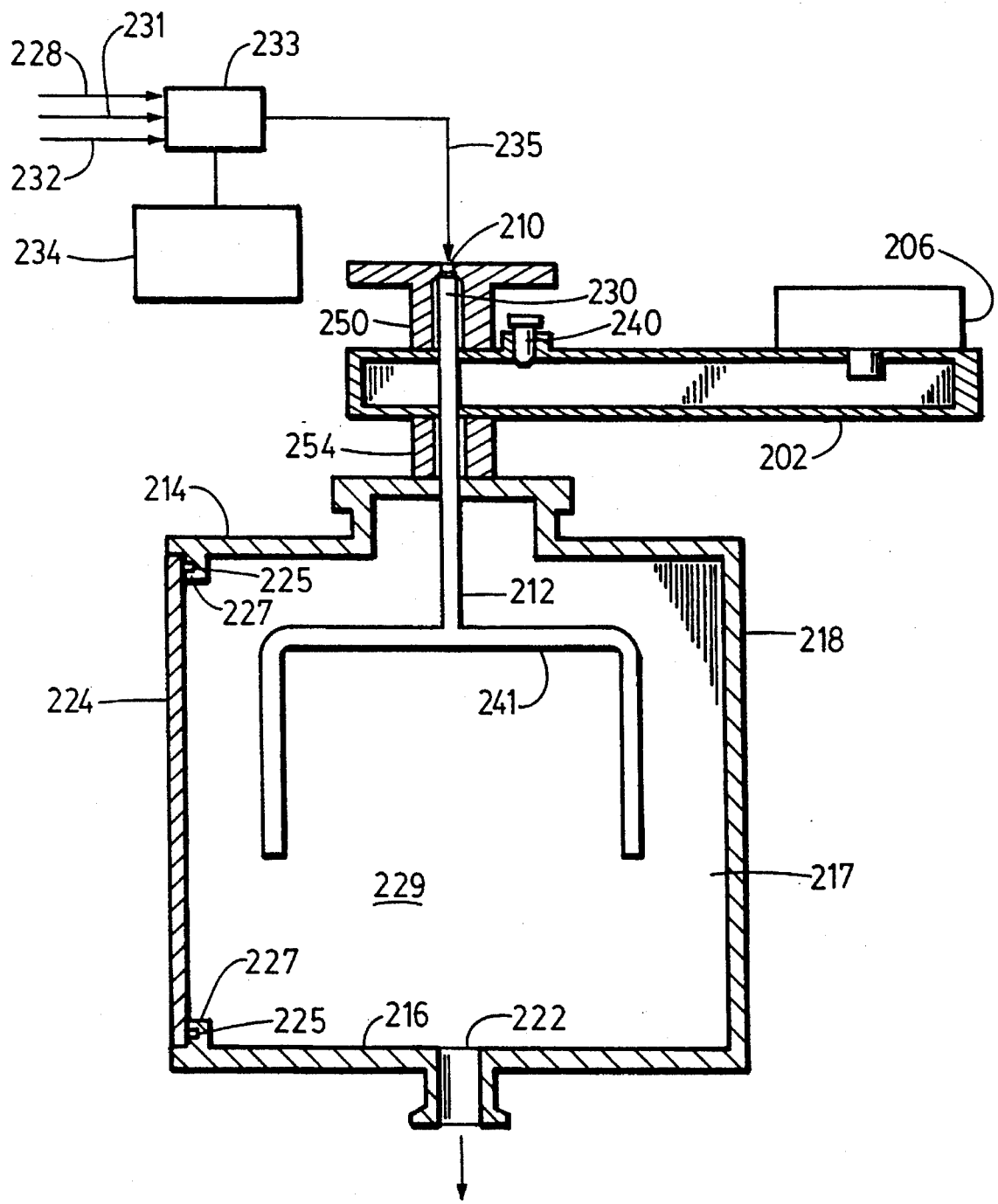
FIG._14.

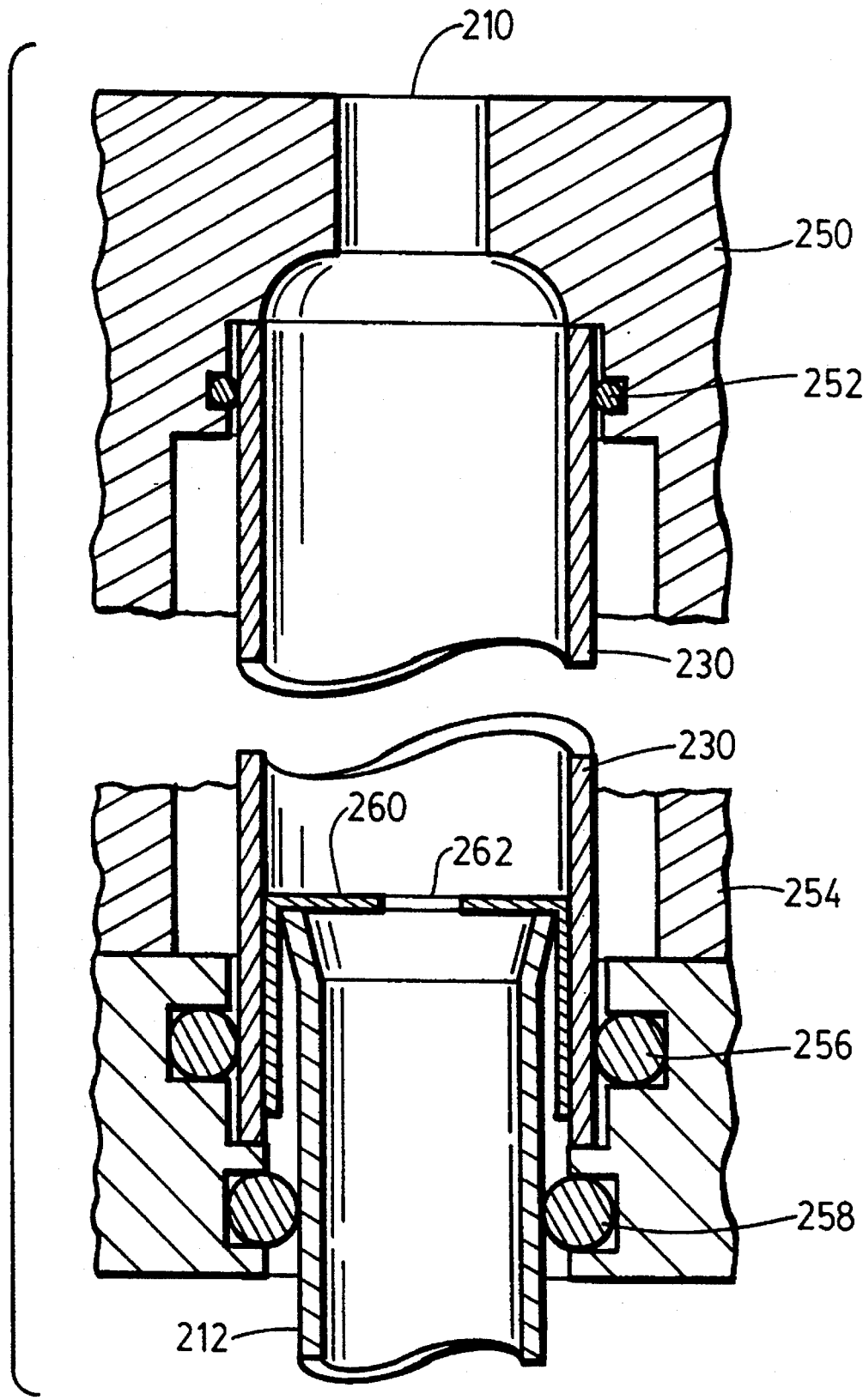
FIG._15.

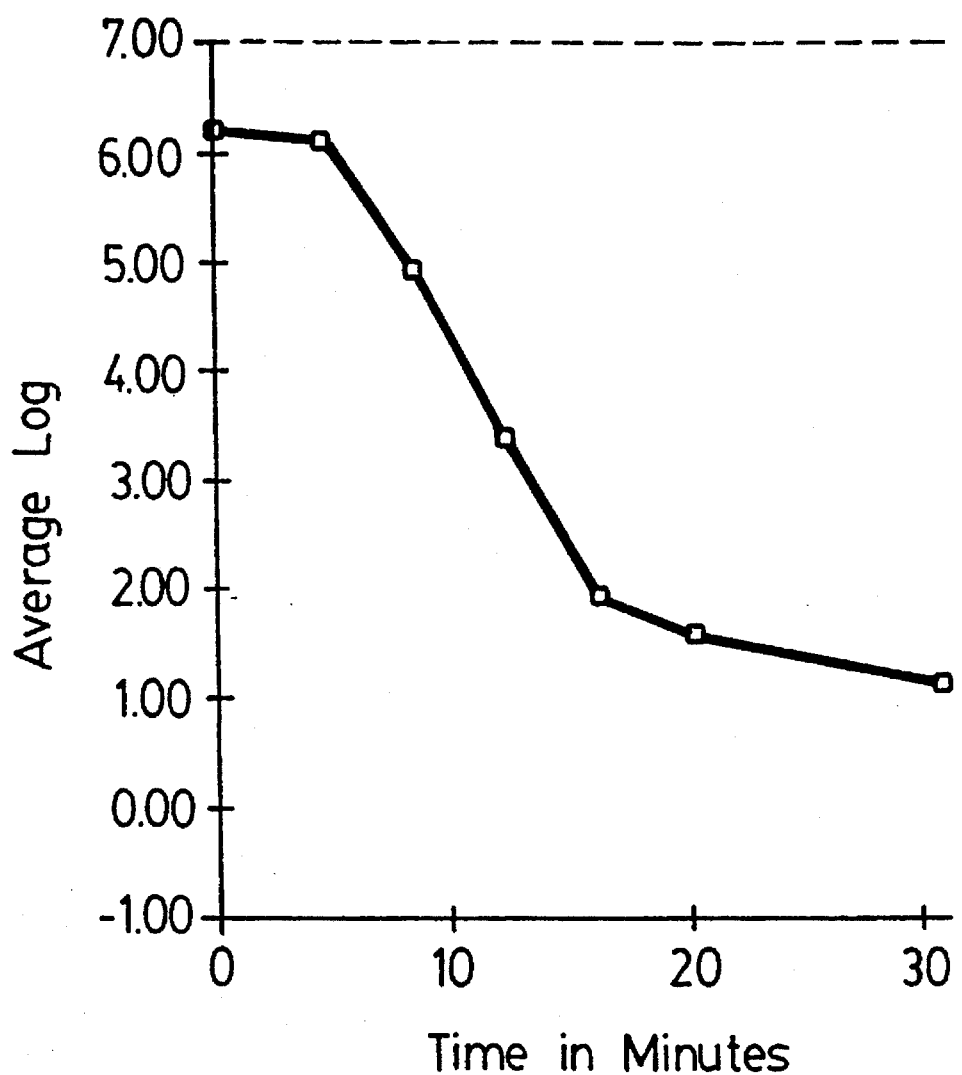
FIG._16.

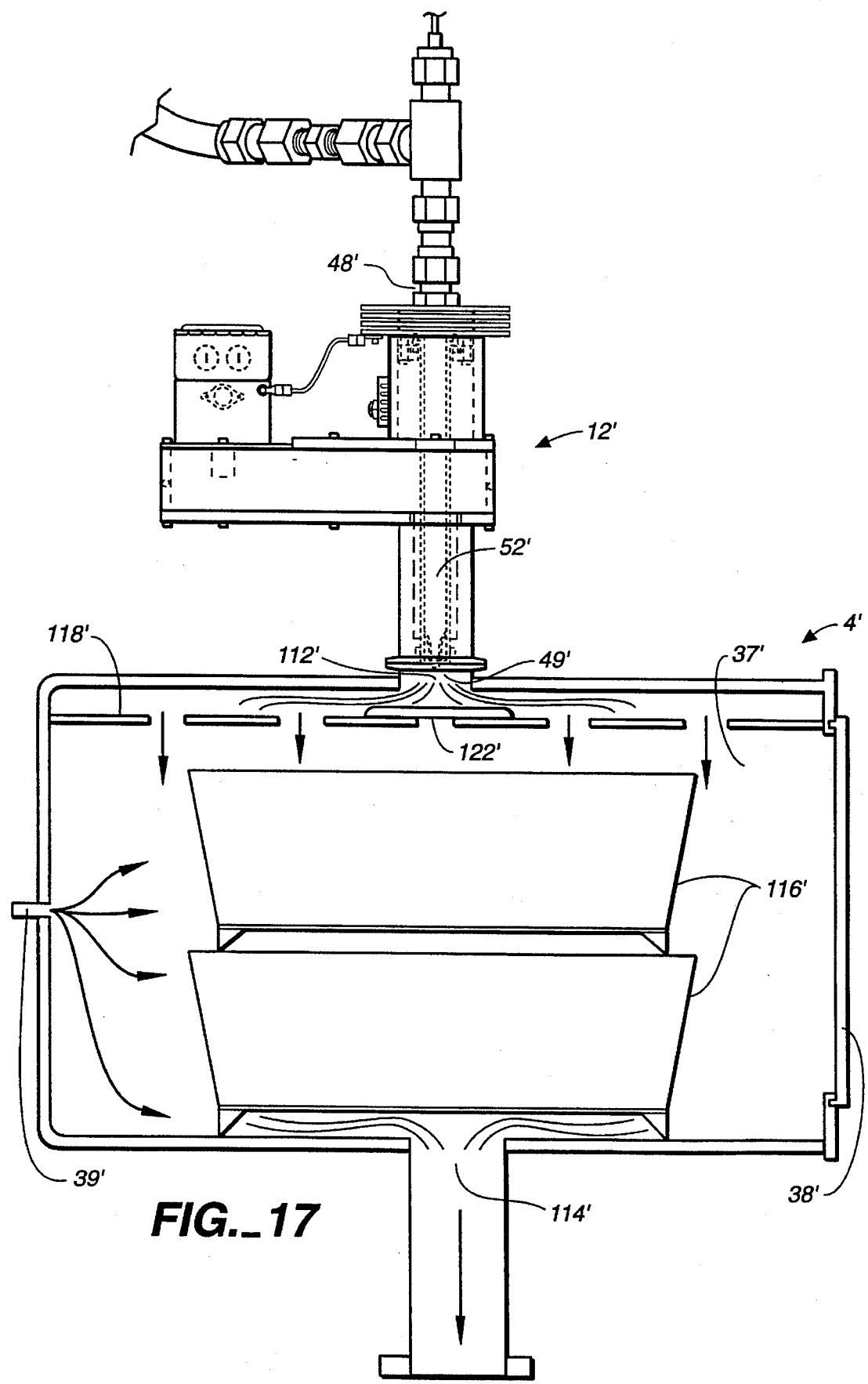
FIG._17

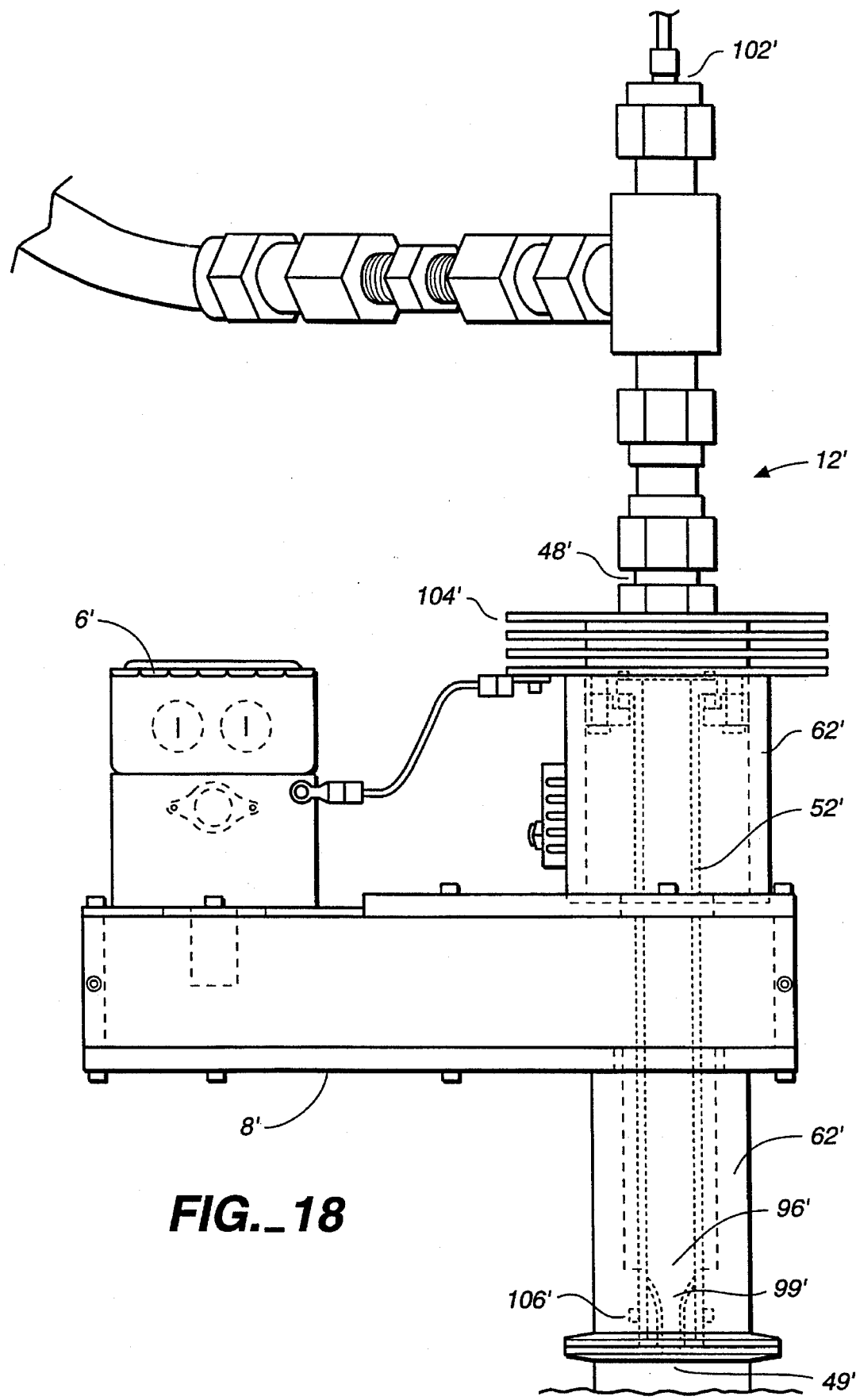
FIG._18

CANISTER WITH PLASMA GAS MIXTURE FOR STERILIZER

This application is a continuation-in-part of copending 08/213,613, filed Mar. 21, 1994 now U.S. Pat. No. 5,472, 664, which is a continuation-in-part of copending application Ser. No. 08/073,653, filed Jun. 7, 1993 now U.S. Pat. No. 5,413, 759, which is a continuation of application Ser. No. 07/817,714, filed Jan. 7, 1992, now abandoned, which is a divisional of application Ser. No. 07/576,292, filed Aug. 31, 1990, now U.S. Pat. No. 5,115,166, which is a continuation-in-part of application Ser. No. 07/475,602, filed Feb. 6, 1990, now abandoned, which is a continuation-in-part of application Ser. No. 07/321,483, filed Mar. 8, 1989, now abandoned.

FIELD OF THE INVENTION

This invention relates to sterilization of articles with gaseous species. In particular this invention relates to a canister containing a gas mixture, which mixture is adapted for use to sterilize articles with a neutral active species of a gas plasma generated from the gas mixture.

BACKGROUND OF THE INVENTION

Various gas sterilization methods have been investigated in the past. Methods using ethylene oxide and other disinfecting gases are widely used for sterilizing a wide range of medical products from pharmaceutical preparations to surgical instruments. Irradiation alone or together with disinfecting gases has also been investigated, as summarized by Russell, A., *The Destruction of Bacterial Spores*, New York: Academic Press (1982).

A sterilizing method must effectively render all microbial organisms non-viable without damage to the article or goods being sterilized and its packaging. However, many disinfecting gases which meet this criteria, such as ethylene oxide and irradiation methods, have been recognized to expose workers and the environment to safety hazards. Recent legislation has been severely restricting the amount of hazardous gases such as ethylene oxide (a suspected carcinogen) in the working environment, or the use of any system or method which produces toxic residues or exhaust products. This has been presenting a major crisis in hospitals and other areas of the health industry.

DESCRIPTION OF THE PRIOR ART

The use of plasma to sterilize containers was suggested in U.S. Pat. No. 3,383,163. Plasma is an ionized body of gas which may be generated by the application of power from different sources. The ionized gas will contact microorganisms on the surfaces of the items to be sterilized and effectively destroy the microorganisms.

Sterilizing plasmas have been generated with a wide variety of gases: argon, helium, or xenon (U.S. Pat. No. 3,851,436); argon, nitrogen, oxygen, helium, or xenon (U.S. Pat. No. 3,948,601); glutaraldehyde (U.S. Pat. No. 4,207, 286); oxygen (U.S. Pat. No. 4,321,232); oxygen, nitrogen, helium, argon, or freon with pulsed pressure (U.S. Pat. No. 4,348,357); hydrogen peroxide (U.S. Pat. No. 4,643,876); nitrous oxide, alone or mixed with oxygen, helium, or argon (Japanese Application Disclosure No. 103460-1983); and nitrous oxide, alone or mixed with ozone (Japanese Application No. 162276-1983). Unfortunately, these plasmas have proven to be too corrosive to articles being sterilized, and particular packaging materials, have left toxic residues on the sterilized articles, or have presented safety or environmental hazards.

Non-plasma gas sterilization procedures have been described using ozone (U.S. Pat. No. 3,704,096) and hydrogen peroxide (U.S. Pat. Nos. 4,169,123, 4,169,124, 4,230, 663, 4,366,125, 4,289,728, 4,437,567, and 4,643,876). These materials have certain process actions which limit their sterilization applications and in some applications are toxic and leave undesirable residues.

Plasma gas sterilizer systems described in U.S. Pat. Nos. 3,851,436 and 3,948,601 comprise a plasma RF generation chamber. A gas plasma produced in the chamber with argon, helium, nitrogen, oxygen, or xenon is passed into a separate sterilization vacuum chamber. U.S. Pat. No. 4,643,876 describes a hydrogen peroxide plasma RF generation chamber which also functions as the sterilizing chamber. Matching networks are required with the RF systems to adjust to the conductivity variations in the plasma generating zone.

SUMMARY OF THE INVENTION

In one aspect of the present invention, a canister is provided that is adapted for use in a plasma induced sterilization process. The canister contains a gas mixture that is pressurized to between about 2200 psig to about 2500 psig. The gas mixture has about 2.0 to 2.4 (v/v) percent hydrogen and about 2.6 to 3.0 (v/v) percent oxygen, and the rest of the gas mixture is noble gas or a mixture of noble gases.

BRIEF DESCRIPTION OF THE DRAWINGS

FIG. 1 is a top view of a plasma sterilizer of this invention.

FIG. 2 is a front view of the plasma sterilizer embodiment of FIG. 1.

FIG. 3 is a cross-sectional view of the plasma sterilizer embodiment of FIG. 1 and FIG. 2, taken along the line 3—3 in FIG. 2.

FIG. 4 is a cross-sectional view of the plasma sterilizer embodiment of FIG. 3, taken along the line 4—4.

FIG. 5 is a cross-sectional view of tube 54 taken along line 5—5 in FIG. 3.

FIG. 6 is a cross-sectional view of tube 58 taken along line 6—6 in FIG. 3.

FIG. 7 is a cross-sectional view of tube 56 taken along line 7—7 in FIG. 3.

FIG. 8 is a partial cross-sectional view of the plasma generator tube and assembly of the embodiment of FIG. 1.

FIG. 9 is a partial, fragmentary, cross-sectional detail view of the plasma generator tube of the plasma generator shown in FIG. 8.

FIG. 10 is a cross-sectional view of the waveguide of the embodiment of FIG. 1, taken along the line 10—10 in FIG. 3.

FIG. 11 is a side cross-sectional view of an alternate single waveguide embodiment of the plasma sterilizer of this invention.

FIG. 12 is a cross-sectional view of the waveguide of the embodiment of FIG. 11, taken along the line 12—12.

FIG. 13 is a side cross-sectional view of a multiple magnetron embodiment of this invention.

FIG. 14 is a front cross-sectional view of the multiple waveguide embodiment of the plasma sterilizer of this invention, taken along the line 14—14 of FIG. 13.

FIG. 15 is a partial cross-sectional view of the plasma generator tube and assembly of the embodiment of FIG. 13.

FIG. 16 graphically illustrates a typical survivor curve when practicing the invention using a plasma generated from a gas mixture according to the invention. A biological indicator (here *Bacillus circulans*) was used with the vertical axis being a logarithmic scale of survivors and the horizontal axis being time in minutes.

FIG. 17 is a side sectional view of the plasma sterilizer according to another embodiment of the invention;

FIG. 18 is a detailed, sectional view of the plasma generator as a component of the plasma sterilizer shown in FIG. 17.

DETAILED DESCRIPTION OF THE INVENTION

Hospitals originally relied on disinfectants and steam autoclaves for sterilizing implements. In more recent years, ethylene oxide gas sterilization has made possible the sterilization of packaged articles, drugs, and medical supplies, and hospital systems are highly dependent upon these procedures. However, ethylene oxide is now suspected to be a dangerous carcinogen and a number of new state laws protecting worker safety and the environment are restricting further use of ethylene oxide sterilizers in hospital environments. In addition, ethylene oxide is known to be a dangerous material from several other aspects. In its pure form it is explosive and flammable and therefore requires that all equipment must be so designed as to be classified as non-explosive. The most popular form of the diluted or non-explosive mixtures contains fluorocarbons (Freon), which are no longer environmentally acceptable. Also, because it is a highly suspected carcinogen, which has resulted in stringent regulations by State and Federal authorities regarding protection of worker safety and emissions to the environment, further burdens and restrictions have been placed on the use of ethylene oxide sterilizers in all applications.

Numerous gas plasma sterilizers using a wide variety of gases have been described in the patent literature. A few have been commercially produced. A few have focused on residue contamination problems. The previously described gas sterilizers fail to satisfy current regulatory residue and exhaust emission safety standards of several states because they leave unacceptable residues, produce exhaust emissions which are potentially hazardous to hospital personal, or cause unacceptable destruction of packaging materials. By substituting one hazard for another, they are thus not satisfactory for replacing ethylene oxide sterilizers.

The gas sterilizer of this invention produces a plasma from a gas mixture containing a noble gas, such as argon or helium, together with a nonflammable mixture of oxygen and hydrogen. This mixture can be designated as non-flammable due to the concentration of flammable or combustion supportive gases being below defined levels of flammability, as evidenced in industry accepted standards published by the Bureau of Mines. Reference Bureau of Mines Bulletin 503, "*Limits of Flammability of Gases and Vapors*" and Bulletin 627, "*Flammability Characteristics of Combustible Gases and Vapors*". According to Lewis et al., *Combustion Flame and Explosions of Gases*, Academic Press (1951), the lower limit of flammability of hydrogen in air is 4.00%(v/v).

The exhaust gas products of the gas mixture after use in the sterilization process fully satisfy current environmental and worker safety concerns, as the products of the plasma are almost entirely water vapor, carbon dioxide and non-toxic gases normally found in the atmosphere.

The plasma is produced as a result of an applied electric or electromagnetic field, including any accompanying radiation which might be produced. The electromagnetic field can cover a broad frequency range, and can be produced by a magnetron, klystron, or RF coil. For purposes of clarity of presentation and not by way of limitation, the description hereinafter describes the use of a magnetron as the electromagnetic field source, and the use of all other suitable sources of the electromagnetic field required for plasma production are intended to be included in this invention, including without limitation, magnetrons, klystron tubes, RF coils, and the like.

The term "sterilization" connotes a process by which all viable forms of microorganisms are destroyed or removed from an object. Since microorganisms die according to first order chemical kinetics, it is customary to define sterility in terms of "probability of survivors." The practical goal of a sterilization process is therefore measured as a probability (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the sterilizing time of identical conditions would result in a doubling of the exponent of the probability term, for example $10^{-6}$ would become $10^{-12}$.

In use of the canister embodiment of the present invention, a plasma generator and a sterilizing chamber are used with the canister gas mixture. Thus, the canister provides a source of pressurized gas mixture in fluid communication with the plasma generator. For example, U.S. Pat. No. 5,244,629, issued Sep. 14, 1993, the disclosure of which is incorporated by reference, describes a pulsed treatment with one or more pulsed-vacuum cycles where one cycle involves exposing the article to be sterilized to a neutral active species of a gas plasma. This gas plasma may be generated from the inventive gas mixture as is hereinafter further described and exemplified.

Turning to FIG. 1, a top view is illustrated with FIG. 2 illustrating a front view of a single waveguide plasma sterilizer embodiment of this invention. The plasma sterilizer has a plasma generator 2 and a sterilizing chamber 4. The plasma generator 2 comprises an electromagnetic field generator such as a magnetron 6 and a waveguide 8 which directs the electromagnetic field. The plasma source gases are directed into plasma generating and delivering tubes 10, 12, and 14 by feeder tubes from gas delivery tubes 16, 18, and 20 leading from the control valve complex 22.

Individual gases are fed from one, or a plurality of pressured gas canisters, in which substantially the same, premixed gas composition is contained. Typical initial pressures are in the range of about 2200 to about 2500 psig. The cylinder is replaced when the pressure drops to about 50 to 100 psig (about 350–700 kPa).

For example, the premixed gas mixture can be stored under pressure in a standard gas cylinder equipped with a valve and a connecting fitting as specified by the Compressed Gas Association. The cylinder pressure can be reduced and regulated by using a standard, conventional gas regulator, which may be mounted to the gas cylinder by a mating CGA fitting. The gas will then flow during practice of the sterilizing method at the desired rate from the regulator to the sterilizer through conventional tubing connected with conventional gas tight fittings.

The preferred gas concentrations of the premixed gases in the gas mixture avoid the potential problem of flammability otherwise possible with an oxygen/hydrogen gas mixture in a noble gas carrier. Nevertheless, although these preferred concentrations are relatively low, the mixture is still useful as the source gas for a plasma formed species having sporicidal activity, as will be exemplified hereinafter.

The optimum gas mixture is about 2.2±0.2 (v/v) percent hydrogen, about 2.8±0.2 (v/v) percent oxygen, and the balance argon or helium, with this mixture being provided from a single container, such as a single pressurized gas canister. Other noble gases could be used (neon, xenon, krypton), but they are less preferred due to expense. Unlike prior art sterilizers with a plurality of different pressurized gas sources designed to be fed through regulating and sensing components, the present invention represents a simpler apparatus since it eliminates such multiple regulating and sensing components required for feed lines from different gas cylinders. Consequently, overall operating performance and reliability are enhanced by eliminating the possibility of incorrect mixture proportions that could result from component failures or operator error. Additionally, routine operating costs are reduced and maintenance simplified.

Such a premixed gas composition of the invention may be fed by inlet line 26. The operation of the control valves in valve complex 22 is controlled by the central processing unit (CPU) 28 by standard algorithms or logic code or operating software. The control valves and CPU can be any of the conventional, standard devices used for gas flow control in plasma generating equipment.

The sterilizing chamber 4 may comprise top plate 30, side plates 32 and 34, bottom plate 36, back plate 37, and front sealing door 38 through which articles or materials to be sterilized are placed in the chamber. The plates are shown attached together in a sealed relationship to form a vacuum chamber, such as by welding. The door 38 is secured in a sealed relationship with the sterilizing chamber. It is attached to the chamber in a practical manner such as tracts or hinges at the top, side, or bottom with, in the case of apparatus shown, conventional hinge pins (structure not shown) to swing against abutting surfaces and an O-ring seal 40 (FIG. 3) of the side, top, and bottom plates, where the pressure difference between the internal chamber vacuum pressure and the surrounding atmospheric pressure holds it tightly in place. However, the door could also be constructed to slide open and to be closed.

The plates and door can be made of any material having the strength required to withstand the external atmospheric pressure when the chamber is evacuated. Stainless steel or aluminum plates and door can be used. The internal surface material of the chamber is critical and greatly affects the number of killing species available in the chamber. One useful material is pure (98%) aluminum which can be applied either as a liner or as a flame-sprayed coating on all internal walls of the stainless steel chamber. An alternate material is nickel. However, we prefer to coat the chamber interior with an inert polymer coating (e.g. Teflon).

The gases are exhausted from the sterilizing chamber through exhaust outlet port 42 to a conventional vacuum pump system (not shown).

FIG. 3 is a top cross-sectional view of the plasma sterilizer embodiment of FIG. 1 and FIG. 2, taken along the line 3—3 in FIG. 2. FIG. 4 is a side cross-sectional view of the plasma sterilizer embodiment of FIG. 1 and FIG. 3, taken along the line 4—4 in FIG. 3. Each of the plasma generators 10, 12, and 14 comprise an inlet cap 44 with a gas inlet port 48 leading to a respective gas generator tube 51, 52, or 53 leading through the waveguide 8. In the waveguide 8, the gases are energized and convert in tubes 51, 52, and 53 to a plasma. The gas generator tube directs the plasma flow into the gas distribution tubes 54, 56, and 58 from which the plasma is fed into the sterilizing chamber 60. The gas generator tubes are enclosed in tubular metal cooling tubes 62 and 64. The caps 44 and the cooling tubes 62 and 64 are preferably provided with groves or cooling fins (not shown) in a conventional manner to increase their efficiency in removing heat from gas generator tubes. The distal ends of the gas distribution tubes 54, 56, and 58 are supported by spring-biased end supports 66 mounted on sideplate 32, but could be modified for gas distributor plenum designs, as known in the art.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamp or latch devices can be used to insure closure of the door before chamber evacuation is initiated.

FIG. 5, FIG. 6, and FIG. 7 are cross-sectional views of gas distribution tubes 54, 58, and 56, respectively, showing angular positions of the gas distribution outlet ports. The outlet ports are positioned to provide plasma flow to all lower portions of the sterilizing chamber 60 where articles to be sterilized are placed. Tube 54 shown in FIG. 5 is placed adjacent back plate 37 and directs plasma gases downward and toward the lower center of the chamber through outlet ports 70 and 72, respectively. Tube 58 shown in FIG. 6 is placed adjacent the door 38 and directs plasma gases downward and toward the lower center of the chamber through outlet ports 74 and 76, respectively. Tube 56 shown in FIG. 7 is placed in the central portion of the chamber 60 and directs plasma gases laterally downward through outlet ports 78 and 80. The outlet ports shown for the distribution tubes are representative and can be changed to any other configuration which achieves optimal plasma distribution to the sterilizing zone or zones of the chamber. Although only one angular arrangement is shown, each tube can have more than one angular set of outlet ports, each having different angles, along the length of the tube, as desired. The choice of outlet port angles and locations should be selected in view of how the articles to be sterilized are to be placed in the chamber and the type of article to be sterilized.

The plasma is preferably directed through a change of direction before discharging it into the sterilizing chamber. The flow of plasma thus impinges on internal surfaces of the gas distribution and sterilizing chamber, thereby cooling it and evenly distributing it. This also prevents direct impingement of hot plasma onto the articles being sterilized, which greatly reduces the oxidation of sensitive packaging materials by the activated oxygen atoms in the plasma.

FIG. 8 is a partial top cross-sectional detail fragmentary view of plasma generator tube 12 of FIG. 3, and FIG. 9 is a more detailed view of the plasma generator tube outlet assembly shown in FIG. 3. The gas fed to the inlet port 48 flows in the passageway 86. The gas mixture passes into the proximal end of the tube 52 and through the excitation zone 87 within the waveguide 8 where the plasma is formed. The proximal end of the plasma generator tube 52 is supported on cylindrical projection 88. O-ring 90 or another type of seal forms a gas-tight seal therewith, thereby maintaining a reduced pressure in the tube 52 and preventing leakage of atmospheric gas into the system.

In this sectional view, an optional plasma starter ionizer is shown. The tip 81 is connected by an insulated conduit 83 (shown schematically) to a power supply 85 which can be powered with a standard 115 V AC power source. A ground conduit 89 from the power supply connects to the gas inlet cap 44. The electric field ionizes a portion of the gas molecules flowing from opening 48 through passageway 86, the ionized gases quickly supporting a plasma as the gases pass through the zone 87. The ionizer can be placed in any of the inlet gas passageways of any of the embodiments of this invention.

Referring to FIG. 9, the outer surface 92 of the distal end of the plasma generator tube 52 is tapered inward and is sealed by O-ring 94 or other form of seal with the backplate 37. The distal end of tube 52 has increased thickness and forms a smooth surfaced venturi restriction 96 of reduced cross-sectional area. Cap 98 positioned on the proximal end of plasma distribution tube 56 has a preselected restrictive opening 99 of further reduced cross-sectional area. These restrictions are critical aspects of the preferred embodiment of this invention, creating a pressure difference between the low pressure plasma generating zone 87 and the vacuum pressure in the distribution tube 56 and sterilizing chamber 60.

The diameter of the restriction diameter 99 is selected to maintain a desired back pressure. This pressure provides optimum energy consumption and plasma generation with the gas mixture and is a major factor for the production of a high yield of plasma at a minimum temperature and with the minimum power requirement achieved with the device of this invention. We prefer to maintain the gas pressure in the plasma generating chamber at 0.01 to 50 torr, preferably at 0.1 to 15 torr. For most operating parameters, the restriction 99 can have a diameter of from about 4.82 to about 8.00 mm and preferably from about 6.28 to about 6.54 mm.

FIG. 10 is a cross-sectional view of the waveguide of the embodiment of FIG. 1, taken along the line 10—10 in FIG. 3. The waveguide is formed of top and bottom plates 100 and 102, side plates 104 and 106 (FIG. 3), and end plates 108 and 110, welded or bolted together. A single magnetron rod 112 is placed in the end of the waveguide 8. The plasma generating tubes 51, 52, and 53 are positioned in the waveguide 8. The positions of the plasma generating tubes are selected to provide maximum conversion of the electromagnetic field energy to plasma. Tube 53 is positioned in a zone to interact with a third of the field and not with zones of the field which will interact with tubes 51 and 52. Tube 52 is positioned in a zone to interact with a third of the field (half of the remaining field) and not with the field zone which will interact with tube 51. Tube 51 is positioned to interact maximally with the remainder of the field. With this configuration, a single magnetron can be used to generate plasma with a plurality of gas generating tubes. The precise placement of the tubes which will accomplish this result will depend upon the dimensions of the wave guide and the wavelength or frequency of the energizing wave.

Three tubes have been shown in FIG. 10 by way of example and not by way of limitation. Any number, odd or even, of tubes can be used up until the total power of the electromagnetic field is absorbed.

FIG. 11 is a front cross-sectional view of an alternate single wave guide embodiment of the plasma sterilizer of this invention. Three plasma generating units 120 are positioned above the sterilizing chamber 122 defined by upper plate 124, lower plate 126, back plate 128, back plate 130, and side plates 128 and 132. The door plate (not shown) can be mounted to the front of the chamber as described above with respect to FIG. 2 and FIG. 3 and forms a sealed engagement with the front edges of the chamber walls. The gases are exhausted from the chamber through exhaust ports 136 in the floor plate 126.

The plasma generators comprise an inlet port for the gas mixture leading to the plasma generating tubes 139, 140, and 141 positioned in the waveguide 142 where the gases are energized and converted to a plasma. The plasma is directed by the plasma distributors 144 to the interior of the sterilizing chamber 122. Each plasma distributor 144 can have a T-configuration described below in detail with respect to the embodiment of FIG. 14. The distributor can have any shape and size which distributes the plasma gases uniformly throughout the sterilizing chamber. The plasma generating source in this embodiment is a magnetron 146 positioned at the end of the waveguide 142.

FIG. 12 is a cross-sectional view of the waveguide of embodiment of FIG. 11, taken along line 12—12 in FIG. 11. The waveguide is formed of top and bottom plates 150 and 152 (FIG. 11), side plates 154 and 156, and end plates 158 and 160, welded or bolted together. A single magnetron rod 162 is placed in the end of the waveguide 142. The plasma generating tubes 139, 140, and 141 are positioned in the waveguide 142. The positions of the plasma generating tubes are selected to provide maximum conversion of the electromagnetic field energy to plasma. Tube 141 is positioned in a zone to interact with a third of the field and not with zones of the field which will interact with tubes 140 and 139. Tube 140 is positioned in a zone to interact with a third of the field (half of the remaining field) and not with the field zone which will interact with tube 139. Tube 139 is positioned to interact maximally with the remainder of the field. With this configuration, a single magnetron can be used to generate plasma with a plurality of gas generating tubes.

The precise placement of the tubes which will accomplish this result will depend upon the dimensions of the wave guide and the wavelength or frequency of the energizing wave. Three tubes have been shown in FIG. 12 by way of example and not by way of limitation. Any number, odd or even, of tubes can be used up until the total power of the electromagnetic field is absorbed.

The detailed construction of the plasma generator tube and plasma distribution tube seals and flow restrictors have the same configuration as the corresponding elements in the embodiment of FIG. 11 and are described in greater detail hereinabove in conjunction therewith.

FIG. 13 is a front cross-sectional view of a multiple magnetron embodiment of this invention, and FIG. 14 is a side cross-sectional view taken along the line 14—14 in FIG. 13. Three plasma generators 208 of this embodiment are positioned above the sterilizing chamber cavity 229, each producing a plasma generated from the gas mixture introduced through inlets 210 to a plasma generating tube 230 positioned in the respective waveguides 202. The plasma produced is fed by plasma generating tubes 230 through respective gas distributors 211, 212, and 213 into the sterilizing chamber 229. The distributor tubes can have any length and configuration required for distributing the plasma gases uniformly throughout the sterilizing chamber. Distribution tubes made of non-fragile materials are particularly advantageous. Suitable non-fragile tubes can be made of oxidation resistant metals such as stainless steel. Optimally, they are made of a plasma resistant polymer such as a fluorocarbon polymer, e.g., TEFLON.

The sterilizing chamber 229 is constructed from metal plates welded to form a gas-tight construction which is able to withstand external pressures when the chamber is evacuated. The construction comprises top plate 214, bottom plate 216, back plate 218, side plates 217 and 219. Exhaust ports 222 are mounted in the bottom plate 216. The door 224 is supported by conventional pin hinges or the like (not shown) mounted on the side, top, or bottom of the chamber walls as described above with respect to the embodiment of FIG. 1. The door 224 is held in sealing engagement by atmospheric pressure against the O-ring seal 225 mounted in the flange 227 extending from the side plates 217 and 219, and the top and bottom plates 214 and 216 (not shown). Optionally, additional conventional closure clamp or latch devices can be used to insure closure of the door before chamber evacuation is initiated.

Referring to FIG. 14, the gas mixture is fed to the inlet port 210 by conduit 235 and then to the plasma generating tube 230 where it is energized to form a gas plasma. The control valves and CPU can be any of the conventional, standard devices used for gas flow control in plasma generating equipment. The waveguide 202 guides the electromagnetic waves generated by the magnetron 206 in a pattern which concentrates the electromagnetic energy in a zone in which the plasma generator tube 230 is positioned. A tuning rod 240 can be vertically positioned to tune the electromagnetic waves to provide optimum plasma generation. The gas plasma is then fed to the gas distributor 212 and its Y- or T-distribution section 241. The horizontal distributors have angular outlet ports positioned and with angular displacement as described with respect to the preferred embodiment of FIG. 5, FIG. 6, and FIG. 7. The plasma is directed through a change of direction, for example, 90°, twice before it is discharged into the sterilizing chamber. This prevents direct impingement of hot nascent plasma onto the articles being sterilized, greatly reducing the oxidation of sensitive packaging materials by the activated oxygen atoms in the plasma.

FIG. 15 is a fragmentary, cross-sectional view of the plasma generating tube of the plasma generator shown in FIG. 14, showing details of the tube construction and its connection with the gas distributor tube. The tube 230 is held in a sealed engagement with the heat radiating cap 250 by O-ring 252 or a similar seal. The lower distal end of the tube is also held in a sealed engagement with the lower heat radiator sleeve 254 by an O-ring 256. The proximal end of the distribution tube 212 extends into the distal end of tube 230 and is held in a sealed relationship with the lower heat radiator sleeve by an O-ring 258. Cap 260 is positioned on the proximal end of plasma distribution tube 212 and has a preselected restrictive opening 262 of further reduced cross-sectional area. As described with respect to the embodiment shown in FIG. 9, the restriction is a critical aspect of the invention, creating a pressure difference between the low pressure plasma generating zone and the vacuum pressure in the distribution tube and sterilizing chamber.

The diameter of the restriction diameter 262 is selected to maintain the desired back pressure, as already discussed for restriction 99.

The embodiments of this invention have been presented with three plasma generating units. The number of generating units is not critical, being selected to provide a good plasma distribution in the particular sterilizing chamber used. Any desired number of plasma generators can be used with each sterilizing chamber and are intended to be included within the scope of this invention. It will be also be readily apparent that any number of gas plasma tubes can be positioned to interact with the electromagnetic field generated from a single magnetron with this waveguide configuration, and that other waveguide configurations can be used to achieve this effect. The preferred plasma generating tubes and plasma distributing tubes are made of quartz. However, any other materials with the necessary physical, chemical, and electrical properties for plasma generation in an electromagnetic field can be used for the plasma generating tubes. Similarly, the conduits and tubing used for transport of plasma from the plasma generator to the sterilizing chamber can be any solid material which has the requisite shape and strength and which is resistant to chemical action and degradation by the plasma gases. Suitable transport conduit materials include quartz and other plasma corrosion resistant glasses, stainless steel and other oxidation resistant metals, and oxidation resistant plastics such as fluorocarbon polymers, e.g. TEFLON and the like, and siloxane polymers.

FIG. 17 is a side sectional view of the plasma sterilizer according to another embodiment of the invention. The plasma sterilizer comprises one or more plasma generators 12' connected to a sterilizing chamber 4'. In a preferred embodiment, there are three plasma generators mounted on top of the sterilizing chamber to provide a uniform and adequate distribution of sterilizing gas mixture into the sterilizing chamber.

FIG. 18 is a detailed, sectional view of the plasma generator. Each plasma generator 12' comprises a housing 62' that is mounted onto a top portion of the sterilizing chamber. The housing supports a plasma generator tube 52' that is preferably a quartz tube transparent to microwave. One end of the plasma generator tube 52' is coupled to a gas inlet 48' for receiving a gas or gas mixture from outside the housing 62'. The other end of the plasma generator tube is coupled to an outlet manifold 49' at the bottom of the housing that allows the gas mixture to flow from the generator tube to the sterilizing chamber 4'.

The housing 62' also supports a waveguide 8', a portion of which intersects the plasma generator tube 52'. The waveguide serves to transmit microwave energy from a microwave source, such as a magnetron 6', to the portion of the plasma generator tube inside the waveguide. Typically, the plasma generator tube is positioned at a crest of the standing waves in the waveguide. The initiation of the plasma is facilitated by a striker 102' near the gas inlet. The striker is connected to a high voltage source (not shown). In this way, the gas mixture that flows through the plasma generator tube is energized in the waveguide and converted into a plasma.

The housing 62' and the waveguide 8' assembly are preferably constructed out of a good conductor such as aluminum and designed to minimize microwave leakage outside the assembly. The housing is also able to establish good thermal contact with the plasma generator tube so that it can dissipate heat generated in the plasma. In a preferred embodiment, cooling fins 104' near the top portion of the housing help to improve heat dissipation.

As the gas mixture flows through the generator tube it is converted into a nascent plasma. It then exits via the outlet manifold into the sterilizing chamber. During that passage the nascent plasma is transformed into a cooler gas mixture of essentially neutral species. The conversion is facilitated by routing the gas mixture through a restrictor 99' and the outlet manifold 49'.

The restrictor 99' helps to define the plasma generating tube 52' as a plasma generating chamber distinct from the sterilizing chamber 4'. In a preferred embodiment, the restrictor is formed by a special termination of the plasma generator tube. Near the outlet manifold 49', the generator tube is formed into a dual-wall tube, with the inner tube terminating into a smooth surfaced venturi restriction 96' of reduced cross-sectional area. The outer wall has the same cross-sectional area as the rest of the generator tube. An O-ring 106' around the dual wall portion secures the plasma generator tube in sealed engagement with the housing near the outlet manifold. The dual-wall construction has the advantage of insulating the O-ring from the heat of the plasma flowing in the inner tube.

The restrictor 99', by virtue of its reduced aperture, serves several important functions. First, different optimal pressures can be maintained in the two different chambers. Typically, the plasma generating chamber is maintained at a higher pressure than the sterilizing chamber, the former being optimized for plasma generation and sustenance and the latter being optimized for uniform dispersion of the sterilizing gas. Secondly, and especially in combination with the outlet manifold, the restrictor increases the probability of plasma components colliding into a surface. This physical structure thus promotes the conversion or recombination of charged particles in the plasma into neutral species. Thirdly, harmful ultra-violet ("UV") radiation generated in the plasma in the generator tube only has a small opening through which to escape into the sterilizing chamber.

Referring again to FIG. 17, the sterilizing chamber 4' comprises a sterilizing enclosure 37' with a sealing door 38'. An inlet port 112' at the top of the enclosure is coupled to the outlet manifold 49' of the plasma generator. An exhaust port 114' at the bottom of the sterilizing enclosure is coupled to an external vacuum pump system (not shown). The articles to be sterilized may be placed in baskets 116' inside the sterilizing enclosure. Alternatively, a perforated exhaust panel may be mounted across the enclosure and above the exhaust port to form a platform for supporting articles to be sterilized. Near the top of the sterilizing enclosure and below the inlet port 112', a perforated gas distribution panel 118' is mounted to distribute the gas mixture including the neutral species entering through the inlet port 112' uniformly throughout the sterilizing enclosure. The perforated gas distribution panel is preferably made of rigid and inert material, such as PTFE, tempered glass, stainless steel or stainless steel coated with PTFE. Furthermore, the material should be opaque to UV light. In general, the perforated gas distribution panel 118' should comprise a self-supporting structure, the main function of which is to distribute the in-flowing gas mixture in a uniform manner into the sterilizing enclosure 37'. In this embodiment, the structure from the base of the plasma generator tube 52' to the perforated gas distribution panel 118' can be regarded as forming the outlet manifold 49'.

A second inlet port 39' on a side wall of the sterilizing enclosure allows antimicrobial additives to be introduced as a vapor or liquid from an external source (not shown).

During operation of the plasma sterilizer, the nascent plasma generated in the plasma generating tube 52' emerges via the outlet manifold 49' into the sterilizing chamber 4'. As described before, virtually all of the charged particles generated in the plasma are converted into neutral species as they pass through the restrictor 99' and the outlet manifold 49' (See also FIG. 18). Similarly, the UV radiation generated in the plasma is greatly reduced by the restrictor 99' and the outlet manifold 49'. Thereafter, the gas mixture is made to negotiate through the perforated gas distribution panel 118' before it enters the sterilizing chamber 4' and acts on the article 120' to be sterilized. In a preferred embodiment a disk 122' made of inert material such as PTFE or glass is placed on the top surface of the perforated gas panel directly below the inlet port 112'. The perforated gas distribution plate, especially in combination with the disk 112', serves several functions. Primarily, it disperses and cools the gas mixture uniformly in the sterilizing enclosure. Secondly, it helps to block what little remaining UV radiation that may have been admitted into the outlet manifold 49'. Finally, it provides an additional surface for conversion of the few remaining charged particles in the gas mixture to neutral species. In this manner, by the time the gas mixture reaches the article to be sterilized, the main sterilizing agent contained therein is essentially neutral species generally devoid of undesirable charged particles and UV radiation.

Sterilizing apparatus with which the canister of this invention generates a sterilizing species derived from the canister contained mixture of noble gas (e.g. argon or helium), oxygen, and hydrogen, as is exemplified hereinafter. The sterilization is carried out at a vacuum pressure of from about 0.1 to 150 torr and preferably from 1 to 40 torr. The temperature in the sterilizing chamber is maintained below 63° C., and preferably is from about 38° C. to about 54° C. Under these conditions, effective sterilization is effected without significant deterioration of packaging materials in which articles to be sterilized may be placed.

Plasma sterilization comprises exposing an article to be sterilized to a plasma generated from a gaseous mixture of argon mixed with oxygen and hydrogen at temperatures of less than 63° C., a pressure of from 0.1 to 150 torr, and a treatment time of at least 5 minutes, and preferably from 10 to 15 minutes. For sterilizing packaged goods, the gas mixture from which the plasma is generated most preferably contains about 2.8 (v/v) percent oxygen and 2.2 (v/v) percent hydrogen, the balance being a noble gas.

Packages for sterilization are treated for at least 15 minutes and preferably from 1 to 5 hours. In an alternate embodiment, packaged goods are sterilized by treatment for at least 15 minutes and preferably from 1 to 5 hours with plasma generated from the gas mixture.

A residence time of from 5 to 10 minutes is usually sufficient to sterilize most articles. Clean articles packaged in envelopes or other shapes having porous surfaces allowing easy penetration of the plasma are usually completely sterilized within 60 minutes.

In an optimum method of sterilizing, the articles to be sterilized are placed in the sterilizing chamber, supported by conventional grids which permit the plasma to reach all surfaces of the articles. The chamber is closed, the sterilizing chamber is evacuated, plasma generation is begun, and the plasma is directed into and through the sterilizing chamber.

The plasma components have a short life, and quickly decay to form non-toxic components usually found in air. These are fully acceptable as residues or as exhaust gas components.

A particularly preferred single gas mixture embodiment of the invention was prepared with oxygen, hydrogen, and the balance argon, which was shown to have suitable sporicidal activity, as is exemplified by the following Example 1 and with reference to FIG. 16.

EXAMPLE 1

Biological indicators are characterized preparations of specific microorganisms resistant to a particular sterilization process. They are used to assist in the qualification of the physical operation of sterilization apparatus and to validate a sterilization process for a particular article. They typically incorporate a viable culture of a known species of microorganism, usually spores. Under the right conditions, sterilization can approximate first order kinetics, and thus allow sterilization cycle times to be readily determined. Biological indicators were prepared as follows and used to exemplify the present invention.

Packages for the biological indicators were obtained from Baxter Laboratories as "Plastipeel Pouches." These pouches have an upper sheet of a gas permeable fabric of bound polyethylene fibers ("Tyvek"), which is already sealed on three edges and where the user seals the fourth edge, after insertion of the carrier, to a lower sheet of impermeable clear polyester film ("Mylar"). Filter paper disks (¼ inch diameter Schleicher & Schuell 740E) were used as carriers for spores. Each disk was inoculated with 5 to 6 logs of spores of a viable organism, which was chosen to be *B. circulans*. *B. circulans* is advantageous as the organism as it has been found to have a higher resistance and more stable resistant pattern when compared to prior art organisms such as *B. subtilis* and *B. stearothermophilus*, as described in Ser. No. 08/111,989, filed Aug. 25, 1993, of common assignment herewith.

Exposure intervals for exposure to the sterilizing gas mixture were chosen, and the biological indicators were placed into the sterilizer apparatus. The biological indicators were exposed to a plasma cycle for the selected exposure required time intervals. The plasma generated gaseous mixture was oxygen 2.8 (v/v) percent and hydrogen 2.2 (v/v) percent and the rest argon. A plasma cycle was flowing the gas mixture embodiment at a volume of about 2.2 standard l/min.

After exposing the biological indicators to the sterilizing gas treatment at different times (the wall temperature was maintained at about 95° F.), the indicators were removed and tested for sterility.

Each pouch was cut open and each carrier was aseptically transferred to labelled, individual grind tubes. Each tube was vortexed until the carriers were macerated. Each macerated carrier was serially diluted using standard plate count techniques. The number of surviving spores (if any) were determined under spore growth conditions.

Survivor curves were generated with the number of surviving spores being determined as a function of exposing step time. D-values for the separate components were calculated using linear regression analysis. D-values (decimal reduction) are the time required at a given set of exposure conditions to reduce a specific population by 90%, and are the negative reciprocal of the slope of the line fitted to the graph of the logarithm of the number of survivors versus time.

Following the experimental methodology just described, survival data were determined, as described below.

Three pouches per run were exposed to the plasma phase for one of the following time intervals: 4, 8, 12, 16, 20, or 60 minutes. Three unexposed carriers were used as positive controls. The results for exposures up to 20 minutes are graphically illustrated by FIG. 16, and demonstrate that the "D value" calculated from the straight line portion of the curve was 2.8 minutes with tailing observed after a 4.5 log reduction in population. Plasma phase exposure after 60 minutes did not result in significant additional lethality. These results demonstrate that for the vast majority of infection control applications with known quantity and resistance of pre-processing bioburden contamination, this process will provide sterile articles without compromising the environment, the sterile barrier properties of the package material used to enclose the article, or the functional properties of the article as discussed above.

It is to be understood that while the invention has been described above in conjunction with preferred specific embodiments, the description and examples are intended to illustrate and not limit the scope of the invention, which is defined by the scope of the appended claims.

It is claimed:

1. A canister, adapted for use in a plasma induced sterilization process, the canister containing a gas mixture, the gas mixture being pressurized to between about 2200 psig to about 2500 psig, the gas mixture comprising about 2.0 to 2.4 (v/v) percent hydrogen and about 2.6 to 3.0 (v/v) percent oxygen, and the rest one or more noble gas(es).

2. A sterilization apparatus, comprising:

means for sterilizing articles with a neutral active species of a gas plasma generated from a gas mixture; and, a gas mixture operably connected to the sterilizing means such that gases from the gas mixture can be supplied to the sterilizing means, the gas mixture being pressurized to between about 2200 psig to about 2500 psig, the gas mixture comprising about 2.0 to 2.4 (v/v) percent hydrogen and about 2.6 to 3.0 (v/v) percent oxygen, and the rest one or more noble gas(es).

3. The sterilization apparatus as in claim 2 wherein the gas mixture is contained in at least one canister in fluid association with the sterilizing means.

\* \* \* \* \*